(12) United States Patent
Zvirbliene et al.

(10) Patent No.: US 7,919,314 B2
(45) Date of Patent: Apr. 5, 2011

(54) PROCESS FOR THE PRODUCTION OF MONOCLONAL ANTIBODIES

(75) Inventors: Aurelija Zvirbliene, Vilnius (LT); Alma Gedvilaite, Vilnius (LT); Rainer Ulrich, Kyritz (DE); Kestutis Sasnauskas, Vilnius (LT)

(73) Assignee: Biotechnologijos Institutas, Vilnius (LT)

( * ) Notice: Subject to any disclaimer, the term of this patent is extended or adjusted under 35 U.S.C. 154(b) by 282 days.

(21) Appl. No.: 11/871,215

(22) Filed: Oct. 12, 2007

(65) Prior Publication Data

US 2009/0269371 A1    Oct. 29, 2009

Related U.S. Application Data

(63) Continuation of application No. PCT/EP2006/003420, filed on Apr. 13, 2006.

(51) Int. Cl.
*C07K 16/08* (2006.01)
*C07K 16/30* (2006.01)
*C12N 5/18* (2006.01)

(52) U.S. Cl. ............... 435/339; 435/344.1; 435/346; 530/388.3; 530/388.85

(58) Field of Classification Search .................. None
See application file for complete search history.

(56) References Cited

U.S. PATENT DOCUMENTS

| | | | |
|---|---|---|---|
| 4,722,840 A * | 2/1988 | Valenzuela et al. ......... | 424/192.1 |
| 5,437,951 A | 8/1995 | Lowy et al. | |
| 5,723,287 A | 3/1998 | Russell et al. | |
| 6,150,508 A * | 11/2000 | Murphy et al. ............ | 530/387.1 |
| 6,719,978 B2 | 4/2004 | Schiller et al. | |
| 2003/0099668 A1 | 5/2003 | Bachmann et al. | |

FOREIGN PATENT DOCUMENTS

| | | | |
|---|---|---|---|
| EP | 0330661 | | 9/1989 |
| EP | 1030923 | | 8/2000 |
| WO | WO00/23955 | | 4/2000 |
| WO | WO03/106616 | * | 12/2003 |
| WO | WO2006/045849 | | 5/2006 |

OTHER PUBLICATIONS

Price et al (Tumour Biology, 1998, vol. 19 (supplement), pp. 1-20).*
Campbell (Monoclonal Antibody Technology, 1984, pp. 1-32).*
Clark (Protein Engineering of Antibody Molecules for Prophylactic and Therapeutic Applications in Man, 1993, pp. 4-5).*
Adams, S. E., et al., "Expression vectors for the construction of hybrid Ty-VLPs," Mol. Biotechnol. 1994;1(2):125-135.
Bashir, I., et al., "Generation of a monoclonal antibody to P-glycoprotein peptides using tuberculin-PPD as a carrier," Virchows Arch. 1998;432:279-287.
Bhatnagar, P. K., et al., "Immune response to synthetic peptide analogues of hepatitis B surface antigen specific for the a determinant," Proc. Natl. Acad. Sci. USA 1982;79:4400-4404.
Fitzmaurice, C. J., et al., "The assembly and immunological properties of non-linear synthetic immunogens containing T-cell and B-cell determinants," Vaccine 1996;14)6):553-560.
Gedvilaite, A., et al., "Formation of Immunogenic Virus-like Particles by Inserting Epitopes into Surface-Exposed Regions of Hamster Polyomavirus Major Capsid Protein," Virology 2000;273(1):21-35.
Gedvilaite, A., et al., "Segments of Puumala hantavirus nucleocapsid protein inserted into chimeric polyomavirus-derived virus-like particles induce a strong immune response in mice," Viral Immunol. 2004;17(1):51-68.
Gold, D. V., et al., "Monoclonal Antibody G47 Engineered to be Reactive with Colorectal Tumor Mucin," Hybrid. Hybridomics 2001;20(5):343-350.
Huhle, G., et al., "Comparison of Three Heparin Bovine Serum Albumin Binding Methods for Production of Antiheparin Antibodies," Semin. Thromb. Hemost. 1994;20(2):193-204.
Jurzak, M., et al., "Monoclonal antibodies against different epitopes of peptide hormones: Use of photoreactive analogues in studies on vasopressin," Eur. J. Biochem. 1990;190:45-52.
Kohler, G., et al., "Continuous cultures of fused cells secreting antibody of predefined specificity," Nature 1975:256(5517):495-497.
Morii, M., et al., "Antigenic Characterization of Hantaan and Seoul Virus Nucleocapsid Proteins Expressed by Recombinant Baculovirus: Application of a Truncated Protein, Lacking an Antigenic Region Common to the Two Viruses, as a Sereotyping Antigen," J. Clin. Microbiol. 1998;36(9):2514-2521.
Okumura, M., et al., "Epitope analysis of monoclonal antibody E5/G6, which binds to a linear epitope in the nucleocapsid protein of hantaviruses," Arch. Virol. 2004;149:2427-2434.
Paknejad, M., et al., "Production of monoclonal antibody, PR81, recognizing the tandem repeat region of MUC1 mucin," Hybrid. Hybridomics 2003:22(3):153-158.
Ruo, S. L., et al., "Monoclonal antibodies to three strains of hantaviruses: Hantaan, R22, and Puumala," Arch. Virol. 1991;119:1-11.
Sasnauskas, K., et al., "Yeast Cells Allow High-Level Expression and Formation of Polyomavirus-Like Particles," Biol. Chem. 1999;380:381-386.
Sasnauskas, K., et al., "Generation of Recombinant Virus-Like Particles of Human and Non-Human Polyomaviruses in Yeast Saccharomyces cerevisiae," Intervirology 2002;45:308-317.
Shin, C. Y., et al., "Production and Characterization of Monoclonal Antibodies Against Human Airway Mucins," Hybridoma 1999;18(5):457-463.
Voronkova, T., et al., "Chimeric Bacteriophage fr Virus-Like Particles Harboring the Immunodominant C-Terminal Region of Hamster Polymavirus VP1 Induce a Strong VP1-Specific Antibody Response in Rabbits and Mice," Viral Immunol. 2002;15(4):627-643.

(Continued)

*Primary Examiner* — Karen A Canella
(74) *Attorney, Agent, or Firm* — Shelly Guest Cermak; Cermak Nakajima LLP

(57) ABSTRACT

Provided is a use of a recombinant chimaeric protein as an immunogen in a process for producing a monoclonal antibody, wherein the recombinant chimaeric protein is assembled into a virus-like particles, and includes a foreign protein or peptide or a fragment thereof.

3 Claims, 3 Drawing Sheets

OTHER PUBLICATIONS

Figure 1:
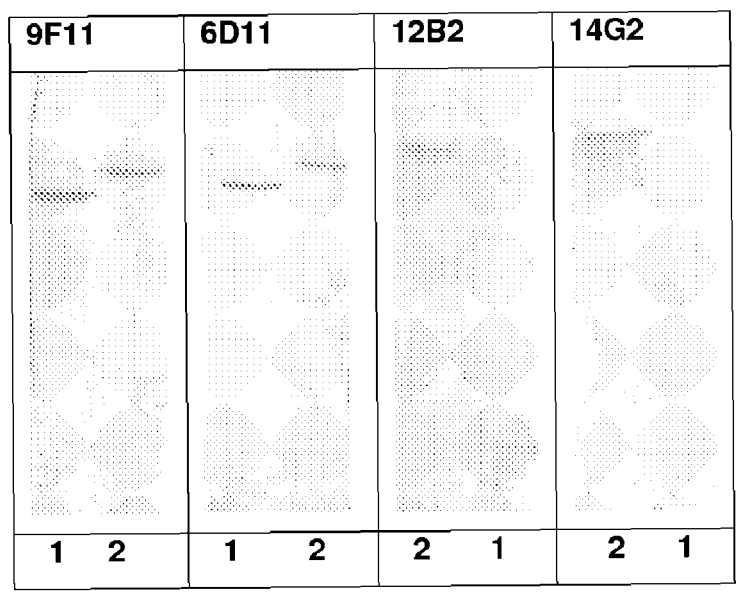

Yoshimatsu, K., et al., "Characterization of the nucleocapsid protein of Hantaan virus strain 76-118 using monoclonal antibodies," J. Gen. Virol. 1996;77:695-704.

Xing, P-X, et al., "Second Generation Anti-Nuci Peptide Monoclonal Antibodies," Cancer Research, American Association for Cancer Research, Baltimore, MD, US, vol. 52, No. 8, Apr. 15, 1992.

Zvirbliene, A., et al., "Generation of monoclonal antibodies of desired specificity using chimeric polyomavirus-derived virus-like particles," J. Immunol. Methods 2006;311(1-2):57-70.

International Search Report for PCT Patent App. No. PCT/EP2006/003420 (Oct. 24, 2006).

* cited by examiner

| 1 | 2 | 3 | 4 | 5 | 6 | 7 | 8 | 9 |

Fig.3.

| A. MAb 5E11 incubated with PUUV hantavirus infected cells. Reactivity with nucleocapsids observed (+). | B. MAb 5E11 incubated with SEOUL hantavirus infected cells. Reactivity with nucleocapsids observed (+). |
|---|---|
| C. MAb 5C5 incubated with PUUV hantavirus infected cells. Reactivity with nucleocapsids observed (+). | D. MAb 5C5 incubated with SEOUL hantavirus infected cells. Reactivity with nucleocapsids observed (+). |

Fig. 4a

| | |
|---|---|
| E. MAb 7A5 incubated with PUUV hantavirus infected cells. Reactivity with nucleocapsids observed (+) | F. MAb 2E6 incubated with PUUV hantavirus infected cells. Reactivity with nucleocapsids observed (+) |
| G. Negative control : non-infected cells incubated with mAb 5E11. No reactivity observed (-). | H. Control MAb 9H3 inbubated with SEOUL hantavirus-infected cells. No reactivity observed (-). |

Fig. 4b

US 7,919,314 B2

```
                    SEQUENCE LISTING

<160> NUMBER OF SEQ ID NOS: 3

<210> SEQ ID NO 1
<211> LENGTH: 20
<212> TYPE: PRT
<213> ORGANISM: Human

<400> SEQUENCE: 1

Pro Ala His Gly Val Thr Ser Ala Pro Asp Thr Arg Pro Ala Pro Gly
1               5                   10                  15

Ser Thr Ala Pro
            20

<210> SEQ ID NO 2
<211> LENGTH: 9
<212> TYPE: PRT
<213> ORGANISM: Human

<400> SEQUENCE: 2

Ser Thr Ala Pro Pro Val His Asn Val
1               5

<210> SEQ ID NO 3
<211> LENGTH: 120
<212> TYPE: PRT
<213> ORGANISM: Puumala hantavirus

<400> SEQUENCE: 3

Met Ser Asp Leu Thr Asp Ile Gln Glu Asp Ile Thr Arg His Glu Gln
1               5                   10                  15

Gln Leu Val Val Ala Arg Gln Lys Leu Lys Asp Ala Glu Lys Ala Val
            20                  25                  30

Glu Met Tyr Pro Asp Asp Val Asn Lys Asn Thr Leu Gln Ala Arg Gln
        35                  40                  45

Gln Thr Val Ser Ala Leu Glu Asp Lys Leu Ala Asp Phe Lys Arg Arg
    50                  55                  60

Met Ala Asp Ala Val Ser Arg Lys Lys Met Asp Thr Lys Pro Thr Asp
65                  70                  75                  80
```

-continued

```
Pro Thr Gly Ile Glu Pro Asp His Leu Lys Glu Arg Ser Ser Leu
            85              90              95

Arg Tyr Gly Asn Val Leu Asp Val Asn Ala Ile Asp Ile Glu Glu Pro
            100             105             110

Ser Gly Gln Thr Ala Asp Trp Tyr
        115             120
```

PROCESS FOR THE PRODUCTION OF MONOCLONAL ANTIBODIES

This application claims priority under 35 U.S.C. §119 to Lithuanian Patent Application No. 2005 043, filed Apr. 13, 2005, and under 35 U.S.C. §120 as a continuation to PCT/EP2006/003420, filed Apr. 13, 2006, the contents of both of which are incorporated by reference in their entireties. The Sequence Listing filed electronically herewith is also hereby incorporated by reference in its entirety (File Name: 060-001_Seq_List_Copy_1; File Size: 2 KB; Date Created: Oct. 12, 2007).

BACKGROUND OF THE INVENTION

1. Field of the Invention

This invention belongs to the field of biotechnology; namely, it describes a process to generate monoclonal antibodies using recombinant chimeric virus-like particles with inserted foreign protein fragments as immunogens. This process can be applied in hybridoma technology to generate new monoclonal antibodies against desired epitopes 2. Background to the Invention To generate new monoclonal antibodies (MAbs) against any antigen, well-known and previously described methods include immunization with:
- recombinant proteins;
- synthetic antigens;
- native proteins isolated from cells, tissues, etc.,
- cell lysates (homogenates);
- eukaryotic cells; or
- viruses, bacteria.

To generate monoclonal antibodies by hybridoma technology, strong immunogens are needed which are capable of activating both B and T cells and eliciting development of IgG antibodies. The immunogens are substances that induce an immune response. It is well documented that strong immunogens are proteins of high molecular weight. Peptides of low molecular weight (up to 50 amino acid long) are typically non-immunogenic. In order to generate monoclonal antibodies against peptides, they should be coupled to a carrier protein.

Different carrier proteins used in hybridoma technology are described: bovine serum albumin (BSA), keyhole limpet hemocyanin (KLH), tuberculin-related purified protein derivatives (PPD) and others [Bhatnagar P K, Papas E, Blum H E, et al., Acad Sci USA. 1982 July; 79(14):4400-4; Bashir I, Sikora K, Foster C S. Virchows Arch. 1998 March; 432(3): 279-87].

Different methods of peptide coupling to the carrier protein are known. The peptide can be coupled to the carrier protein using different chemical reagents. For example, coupling using glutaraldehyde, carbodiimide and other chemical agents is well-known [Huhle G, Harenberg J, Malsch R, Heene D L. Semin Thromb Hemost. 1994; 20(2):193-204.] Photochemical coupling can be also used [Jurzak M, Boer R, Fritzsch G, Kojro E, Fahrenholz F. Eur J Biochem. 1990 May 31; 190(1):45-52.].

An alternative method is generation of synthetic peptides consisting of B and T cell epitopes [Fitzmaurice C J, Brown L E, McInerney T L, Jackson D C. Vaccine. 1996 April; 14(6): 553-60].

The disadvantage of all these methods is that the peptide (or epitope) might be "hidden" inside the carrier protein and therefore might be not accessible to the cells of the immune system, namely, B cells that produce antibodies and are needed to generate hybridomas.

Another disadvantage of all these methods is that it is difficult to generate hybridomas producing antibodies against the peptide but not the carrier protein. As the carrier protein is much larger than the coupled peptide, the carrier contains more B cell epitopes and stimulates B cells more efficiently than the peptide. Therefore, even in the case if the peptide is accessible to B cells, usually the yield of hybridomas producing antibodies against the carrier protein is significantly higher than those producing antibodies against the peptide.

As such, there is a need for new more efficient method of producing monoclonal antibodies that overcomes the problems associated with methods of the prior art. In particular, there is a need for a method that allows the production of monoclonal antibodies against short peptides and non-immunogenic protein sequences for instance.

SUMMARY OF THE INVENTION

Accordingly, in a first aspect, the present invention provides a method for producing a hybridoma capable of producing a monoclonal antibody against a foreign protein or peptide, comprising the steps of:
a) immunizing a non-human animal;
b) harvesting spleen cells from the immunized animal; and
c) hybridising the harvested spleen cells to immortalised cells to obtain a hybridoma;
wherein the immunization of the non-human animal is performed with a recombinant chimaeric protein which is assembled into a virus-like particle and which includes a the foreign protein or peptide or a fragment thereof.

In a second aspect the present invention provides a method for producing a monoclonal antibody against a foreign protein or peptide, comprising the steps of the method for producing a hybridoma stated above, and the further steps of propagating the hybridoma, and obtaining the antibody from the hybridoma.

In a third aspect, the present invention provides hybridomas and monoclonal antibodies produced by the method of the present invention.

In a fourth aspect, the present invention provides the use of a recombinant chimaeric protein as an immunogen in a process for producing a hybridoma capable of producing monoclonal antibodies, wherein the recombinant chimaeric protein is assembled into a virus-like particle, and includes a foreign protein or peptide or a fragment thereof.

In a fifth aspect the present invention provides the use of a recombinant chimaeric protein as an immunogen in a process for producing a monoclonal antibody, wherein the recombinant chimaeric protein is assembled into a virus-like particles, and includes a foreign protein or peptide or a fragment thereof.

In a sixth aspect the present invention provides a method for producing/obtaining a monoclonal antibody against a foreign protein or peptide, comprising the step of immunizing a non-human animal with a recombinant chimaeric protein wherein the recombinant chimaeric protein is assembled into a virus-like particles, and includes a foreign protein or peptide or a fragment thereof.

The use of recombinant chimeric proteins, for example, yeast-expressed viral proteins with inserted foreign protein fragments (epitopes) at certain sites of the molecule and assembled to virus-like particles, has not previously been described as a means to generate monoclonal antibodies against the inserted foreign peptides.

Surprisingly, it has been found that a recombinant chimaeric protein containing a fragment of a foreign protein or peptide and assembled into a virus-like particle is a highly efficient immunogen for eliciting B cell humoral responses against peptides, proteins or fragments thereof. This discovery can especially be applied to the production of monoclonal antibodies via hybridoma technology. Moreover, the method allows the relatively efficient production of hybridomas and thus monoclonal antibodies, against short peptides and non-immunogenic protein sequences. In particular, it is noted that the present invention is more efficient at generating antibodies against the foreign protein or peptide than the prior art methods.

Further, when the recombinant chimaeric proteins contain larger fragments of the foreign protein or peptide, it has been discovered that these fragments are correctly folded, resulting in the development of antibodies directed to the epitopes present in the native protein, against which a monoclonal antibody is desired.

While the present invention can particularly be applied to the production of monoclonal antibodies through the production of hybridomas, other techniques directed to the immortalization of B cells can be used to generate monoclonal antibodies. For example, the use of Epstein-Barr virus to immortalize human B cells is a technique generally known in art.

In one embodiment according to the invention, the method further comprises an additional step of providing at least one immunization boost to the non-human animal.

The method of the present invention is preferably used when the foreign protein or peptide or fragment thereof, against which an antibody is required, when used alone to immunize the non-human animal does not produce a humoral immune response. The term "humoral immune response" refers to those mediated at least in part by antibody e.g. soluble antibody.

In one aspect of the present invention the immunizing step produces an antibody response in the non-human animal against the foreign protein or peptide or the fragment thereof. In a further aspect, the immunizing step produces an antibody response in the non-human animal only against the foreign protein or peptide or the fragment thereof.

In one aspect of the method according to the present invention the foreign protein or peptide or the fragment thereof is natively folded in the virus-like particle. Still further, it may be exposed on the surface of the virus-like particle. The term "natively folded" indicates that the protein is folded in the way it would be when it is in its wild-type form.

According to the present invention the recombinant chimaeric protein contains a fragment of the foreign protein or peptide against which the antibodies are required. The remaining sections of the chimaeric protein are not limited in length or sequence provided that the recombinant chimaeric protein is capable of self-assembly to form a virus-like particle. In particular, the recombinant chimaeric protein may comprise at least part of a viral capsid protein sequence. Preferably, the viral capsid protein is a hamster polyoma capsid protein, in particular the major capsid protein, VP1.

In a preferred aspect of the invention, the fragment of the foreign protein or peptide is inserted into the capsid protein sequence at a position that allows for integration of foreign sequences while maintaining the ability of the capsid protein to assemble into a virus-like particle. In a particularly preferred aspect of the present invention the fragment of the foreign peptide is inserted into site 1 (between amino acids 80 and 89) and/or site 4 (between amino acids 288 and 295) of the major capsid protein VP1, of the hamster polyoma virus.

In one embodiment of the invention, the fragment of the foreign protein or peptide is from 5, 6, 7, 8 or 9 amino acids to 300 amino acids in length. In particular, the present invention is useful in methods where the fragment is from 5, 6, 7, 8 or 9 amino acids to 50 amino acids in length. In further aspects of the invention the fragment is from 5, 6, 7, 8 or 9 to 44 amino acids in length, to 25 amino acids in length or to 10 amino acids in length.

In one embodiment of the present invention the monoclonal antibody is an IgG antibody.

Preferably the peptide is incapable of generating a humoral B cell response when the non-human animal is immunized with the peptide alone i.e. without it being chemically coupled to a carrier, or as part of a recombinant protein. The term "alone" in the context of the present application does not exclude the peptide being used in, for example, a saline solution or a solution comprising an adjuvant. It refers to the foreign protein, peptide or fragment thereof being used in its native state i.e. not incorporated into a virus-like particle. More preferably the peptide is incapable of generating a humoral B cell response when the non-human animal is immunized with the peptide coupled to a non-viral carrier such as BSA.

In one example of the present invention, a hybridoma is produced which is capable of producing monoclonal antibodies against a Muc1 epitope. In another example of the present invention, a hybridoma is produced which is capable of producing monoclonal antibodies against a hantavirus nucleocapsid protein. Further the present invention relates to monoclonal antibodies obtainable from these hybridomas.

Still further, the invention relates to an antibody which binds to human mucin at an epitope within SEQ ID No. 2 (i.e. an antibody which binds to human mucin protein at an epitope within the sequence of the Muc1 peptide) and an antibody which binds to hantavirus nucleocapsid protein at an epitope within SEQ ID No. 3 (i.e. an antibody which binds to an epitope between amino acid residues 1 to 120 of the N-terminal 120 amino acids of hantavirus nucleocapsid protein). Preferably these antibodies are IgG antibodies. More preferably the IgG antibody is of a subclass selected from IgG1, IgG2a or IgG2b.

In further aspects the invention relates to the following:

A method to produce monoclonal antibodies, which includes immunization of certain mouse strain, at least one boost immunization, hybridization of spleen cells, propagation and cultivation of hybrid clones, which differs in the following: the immunization is performed by injecting into mice the solution of recombinant chimeric proteins harbouring inserted fragments of foreign proteins and capable to self-assemble to virus-like particles.

A method as defined in the paragraph above which differs in the following: in order to generate certain monoclonal antibodies virus-like particles are used that contain fragments of proteins against which monoclonal antibodies are intended to produce; these fragments are inserted into defined sites of the virus-like particle.

The present invention also relates to the use of recombinant chimeric virus-like particles harbouring inserted fragments of foreign proteins as immunogens to generate hybridomas.

BRIEF DESCRIPTION OF DRAWINGS

FIG. 1 shows Western blotting picture where recombinant proteins VP1 and VP1/Muc were immunostained with MAbs produced by hybridomas 12B2 and 14G2.

FIG. 2 illustrates the immunogenicity of chimeric protein VP1/VR120.

FIG. 3 illustrates the ability of MAbs produced by hybridomas 7A5, 5E11, 5C5 and 2E6 to recognize full-length hantavirus nucleocapsid protein.

FIGS. 4a and 4b illustrates the ability of MAbs produced by hybridomas 5E11, 5C5, 7A5 and 2E6 to recognize native viral nucleocapsid in hantavirus-infected cells.

The invention will now be described in further detail, and with reference to the accompanying drawings and Examples.

DESCRIPTION OF THE PREFERRED EMBODIMENTS

The term "virus-like particle" is well known in the art and refers to a structure resembling a virus particle. It is in fact an association of proteins of one virus that resembles the virus but does not contain any replicating nucleic acid and is by itself thus not capable of causing an infection.

The term "foreign protein or peptide" refers to a protein or peptide sequence which is derived from a different source from that from which the remaining VLP sequence is derived. Thus a DNA coding for the foreign protein or peptide is inserted into a sequence coding for the rest of the virus-like particle leading to synthesis of a recombinant chimaeric protein i.e. a hybrid protein.

The expression of hamster polyoma virus major capsid protein in yeast as well as the properties of virus-like particles (VLPs) with inserted fragments of hantavirus nucleocapsid proteins were described previously [Gedvilaitė A., Frommel C., Sasnauskas K., et al., Virology. 2000, v. 273, n. 1, p. 21-35]. In the description of Patent EP 1030923 (publ. 2000) it is indicated that hamster polyoma virus major capsid protein forms virus-like particles that might be used in medicine and veterinary science as tools for gene therapy, vaccine development and diagnostics. However, the use of these recombinant proteins to generate monoclonal antibodies of desired specificity was not described or suggested.

The inventors have used the method of the present invention to generate hybridomas capable of producing monoclonal antibodies against human mucin protein and the hantavirus nucleocapsid protein.

Hybridoma cell lines HM02, HM03, G47, BCP7-10, PR81 producing MAbs against human mucin are described in the literature. Hybridomas HM02 and HM03 differ from those described here by these features: 1) they were obtained by immunizing with mucin purified from sputum, 2) they produce antibodies of IgM class against mucin [Shin C Y, Lee W J, Kim D J et al, Hybridoma. 1999; 18(5):457-463]. Hybridoma G47 differs from those described here, since it was obtained by immunizing with mucin purified from gut tissue [Gold D V, Cardillo T M Hybrid Hybridomics. 2001; 20(5-6):343-350]. Hybridomas BCP7-BSP10 were obtained by immunizing with a peptide corresponding to MUC1 protein sequence PAHGVTSAPDTRPAPGSTAP (SEQ ID No: 1) chemically coupled to the carrier protein [Xing P X, Prenzoska J, Quelch K, McKenzie I F, Cancer Res. 1992 15; 52(8):2310-2317]. Hybridoma PR81 producing MAbs of IgG1 subtype against human mucin was generated by immunizing with homogenized tumour tissue [Paknejad M, Rasaee M J, Tehrani F K et al, Hybrid Hybridomics. 2003; 22(3):153-158].

Hybridoma cell lines ECO2, ECO1, BDO1, C16D11, F23A1, C24B4, E5/G6, DCO3 producing MAbs against hantavirus nucleocapsid protein are described. Hybridomas ECO2, ECO1 and BDO1 were obtained by immunizing with inactivated Hantaan, R22 and Puumala hantaviruses [Ruo S L, Sanchez A, Elliott L H Arch Virol. 1991; 119(1-2):1-11]. Hybridomas C16D11, F23A1, C24B4, E5/G6 were obtained by immunizing with recombinant full-length hantavirus nucleocapsid protein [Yoshimatsu, K., J. Arikawa, M. Tamura et al, J. Gen. Virol. 1996, 77:695-704]. It was determined that hybridoma E5/G6 produces MAb specific to the sequence between amino acid residues 165 and 173 of hantavirus nucleocapsid protein [Okumura M, Yoshimatsu K, Araki K, Arch Virol. 2004; 149(12):2427-2434]. Hybridoma DC03 was obtained by immunizing with recombinant full-length SEQ hantavirus nucleocapsid protein expressed in baculovirus expression system [Morii M, Yoshimatsu K, Arikawa et al, J Clin Microbiol. 1998; 36(9):2514-2521]. The previously described hybridomas differ from those described herein as they were obtained by immunizing with either full-length recombinant hantavirus nucleocapsid protein or viruses but not VLPs harbouring an inserted fragment of hantavirus nucleocapsid protein.

The current invention was aimed at generation of monoclonal antibodies against desired amino acid sequence, epitope or protein fragment.

Investigations performed by the authors of this invention suggested that chimeric recombinant viral proteins assembled to virus-like particles (VLPs) can be used in hybridoma technology to generate monoclonal antibodies against the inserted fragments. It was demonstrated, that immunogens described in the current invention promote development of monoclonal antibodies more efficiently than the analogs described in the prior art.

The method of monoclonal antibody production according to the present invention includes: immunization of certain mouse strain, at least one boost immunization, hybridization of mouse spleen cells, propagation and cultivation of hybrid clones. It differs from the methods of the prior art as the immunization is performed by injecting into mice a solution of recombinant chimeric proteins harbouring fragments of foreign proteins and assembled into virus-like particles. These chimeric proteins are more immunogenic and more efficiently promote development of monoclonal antibodies than previously described immunogens.

In addition, for the generation of particular monoclonal antibodies virus-like particles are used that contain inserted fragments of proteins against which monoclonal antibodies are to be generated. These fragments can be inserted at any position that guarantees the presentation of the inserted sequence on the surface of VLPs and does not disturb the formation of VLPs. These fragments can be inserted at defined sites of the virus-like particle, which allow the exposure of the inserted epitopes on the surface of virus-like particle.

By the method disclosed in the current invention new hybridomas producing monoclonal antibodies against Muc1 peptide (9 amino acid-long sequence STAPPVHNV—SEQ ID No. 2) and a fragment of hantavirus nucleocapsid protein (N-terminal 120 amino acid-long sequence—SEQ ID No. 3) were obtained.

New hybridomas are designated as 12B2, 14G2, 7A5, 5E11, 5C5, 2E6. They are stored at the Laboratory of Immunology, Institute of Biotechnology, Graičiūno g.8, LT-02241, Vilnius, Lithuania, under storage numbers: M0501, M0502, HN0501, HN0502, HN0503, HN0504, respectively. Hybridomas 14G2 and 5E11 were deposited at Deutsche Sammlung von Mikroorganismen und Zellkulturen (DSMZ, located at Mascheroder Weg 1 b, D-38124 Braunschweig. Germany). which is an internationally recognized depositary authority under the Budapest Treaty. on Jun. 22, 2006. The hybridomas 14G2 and 5E11 were deposited under the Budapest Treaty and given accession numbers DSM ACC2788 and DSM ACC2787, respectively.

In order to generate new hybridomas, hamster polyoma virus major capsid protein harbouring inserted foreign fragments (epitopes) and self-assembled to virus-like particles (VLPs) is employed. The following standard previously described procedures are used:

1) Immunization—VLPs were injected subcutaneously into BALB/c mice. Before the injection, VLP solution was mixed with an equal volume of complete Freund's adjuvant;
2) Boost immunization—four weeks later the mice were injected subcutaneously with the same dose of VLPs mixed with incomplete Freund's adjuvant;
3) Four weeks later the mice were injected with the same dose of VLPs without an adjuvant. During immunization, the development of antibodies against the inserted fragment (epitope) in the sera of immunized mice was monitored. The monitoring was performed by a known method—enzyme-linked immunosorbent assay (ELISA).
4) Four-five weeks after the first immunization the development of specific antibodies in serum was determined. Development of specific antibodies indicates the immunogenic efficiency of VLPs, e.g., it confirms if VLPs efficiently stimulate B cells specific to the inserted fragment (epitope);
5) After the 3rd immunization spleen cells were fused with cancer cells, namely, myeloma Sp 2/0 cells, by using polyethyleneglycol (PEG) as a fusion agent (Sigma, USA). This and further procedures were performed according to the previously described procedure used to generate hybridomas [Kohler, Milstein, Nature 1975; 256:495-497].
6) Obtained hybrid cell clones (hybridomas) were tested for their specificity, e.g., it was determined what kind of antibodies they produce. An ELISA assay was used for this purpose. The aim of this testing was to determine if the hybridomas produce antibodies against the inserted fragment;
7) It was evaluated how efficiently the inserted fragment displayed on VLPs stimulates B cells needed to generate hybridomas. The hybridomas were characterized as follows:
   isotype of produced monoclonal antibodies was determined;
   specificity of monoclonal antibodies was studied by ELISA and Western blotting.
8) The hybridomas that were identified to produce antibodies of desired specificity were cloned, propagated and frozen for a further storage;
9) Antibodies produced by the hybridomas were characterized by well-known methods—ELISA and Western blotting.

Thus, recombinant chimeric proteins harbouring inserted foreign protein fragments or epitopes were used for the immunization of mice. Spleen cells of the immunized mice were further fused with myeloma cells to generate hybridomas producing monoclonal antibodies against the inserted sequences. Chimeric proteins assembled to virus-like particles display the inserted sequences on the surface of the protein, therefore, they efficiently promote antibody development.

By the process described above new hybridomas were obtained and their properties were investigated. The hybridomas are stored at the Institute of Biotechnology, Laboratory of Immunology (Vilnius):

1) Hybridoma 12B2, storage number M0501, producing MAb of IgG1 subtype against Muc1 epitope (9 amino acid-long sequence STAPPVHNV—SEQ ID No. 2);

2) Hybridoma 14G2, storage number M0502, producing MAb of IgG1 subtype against Muc1 epitope (9 amino acid-long sequence STAPPVHNV—SEQ ID No. 2);

3) Hybridoma 7A5, storage number HN0501, producing MAb of IgG1 subtype against hantavirus nucleocapsid protein (N-terminal amino acid sequence—SEQ ID No. 3);

4) Hybridoma 5E11, storage number HN0502, producing MAb of IgG1 subtype against hantavirus nucleocapsid protein (N-terminal amino acid sequence—SEQ ID No. 3);

5) Hybridoma 5C5, storage number HN0503, producing MAb of IgG2a subtype against hantavirus nucleocapsid protein (N-terminal amino acid sequence—SEQ ID No. 3);

6) Hybridoma 2E6, storage number HN0504, producing MAb of IgG2b subtype against hantavirus nucleocapsid protein (N-terminal amino acid sequence—SEQ ID No. 3).

Hybridomas 12B2, 14G2, 7A5, 5E11, 5C5 and 2E6 are characterized by the following features.

Morphologic properties. Hybridomas are round-shaped, with a large nucleus. They grow in suspension, are slightly adherent on glass or plastic surface;

Parent cell cultures. Hybridomas were obtained by fusion of spleen cells of the immunized BALB/c mouse (*Mus. musculus*) with mouse (*Mus. musculus*) myeloma cell line Sp2/0.

Cell culture properties. Hybridomas are cultivated under standard conditions. Their growth medium is Dubecco modified Eagl's medium (DMEM) with 2 mM L-glutamine, 200 μg/mL gentamicin and 10% fetal calf serum. Hybridomas are cultivated in glas or plastic flasks for cell culture. The cells are subcultivated every 3-4 days, inoculation dose is 50-100 thousands of cells per milliliter of growth medium. Hybridomas are grown in an incubator in 5% $CO_2$ atmosphere at 37° C. For a long storage, the hybridomas are frozen in fetal calf serum containing 10% DMSO. They are stored in liquid nitrogen. Freezing conditions: $1\times10^6$–$2\times10^6$ cells per milliliter, temperature decrease—1° C./min. until −70° C. After 24 hrs the vials with frozen cells are transferred to liquid nitrogen. For a thawing, the cultures are incubated in a water bath at 37° C. The viability of cells after thawing—70-80%.

Contamination. Hybridoma cultures are free of bacteria and fungi. Mycoplasma test is negative.

Productivity of hybridomas. MAb secretion level in growth medium—10-30 μg/ml. The stability of MAb secretion—up to 15 passages (sub-cultures).

Characterization of the products. Hybridomas 12B2 and 14G2 produce MAbs of IgG isotype, IgG1 subtype, specific to Muc1 epitope (Muc1 epitope is a fragment of human mucin protein). Hybridomas 7A5, 5E11, 5C5 and 2E6 produce MAbs of IgG isotype, specific to hantavirus nucleocapsid protein.

These hybridomas differ from the analogs described previously as they were obtained by using VLPs with inserted particular peptide fragments (epitopes) for the immunization.

Hybridomas 12B2 and 14G2 differ from the analogs described previously—hybridomas producing MAbs against mucin—as they were obtained by immunizing mice with VLPs harbouring inserted Muc1 epitope (9 amino acid-long sequence STAPPVHNV—SEQ ID No. 2). The analogs described previously were obtained by using either synthetic peptides chemically coupled to the carrier protein or full-length mucin or homogenized cells.

Moreover, hybridomas 12B2 and 14G2 differ from the analogs HM02 and HM03 according to the isotype of secreted immunoglobulins.

Hybridomas 7A5, 5E11, 5C5 and 2E6 differ from the analogs described previously—hybridomas producing MAbs against hantavirus nucleocapsid protein—as they were obtained by immunizing mice with VLPs harbouring inserted N-terminal fragment of hantavirus nucleocapsid protein consisting of 120 amino acids (aa)—SEQ ID No. 3:

```
MSDLTDIQEDITRHEQQLVVARQKLKDAEKAVEMYPDDVNKNTLQARQQT
VSALEDKLADFKRRMADAVSRKKMDTKPTDPTGIEPDDHLKERSSLRYGN
VLDVNAIDIEEPSGQTADWY.
```

The analogs described previously differ from hybridomas 7A5, 5E11, 5C5, 2E6 as they were obtained by immunizing mice with either full-length hantavirus nucleocapsid proteins or viruses but not VLPs harbouring a fragment of hantavirus nucleocapsid protein. In addition, analog hybridoma E5/G6 differs according to the MAb specificity—it produces MAbs specific to the sequence aa 165-173 while hybridomas 7A5, 5E11, 5C5, 2E6 produce Mabs specific to the sequence aa 1-120 of hantavirus nucleocapsid protein.

The method to produce new monoclonal antibodies and the properties of new hybridomas are illustrated by the information given below: Examples 1-5, Tables 1-2, FIGS. 1-4.

The method to produce new monoclonal antibodies and their properties are described in more details in the examples given below.

EXAMPLE 1

The use of chimeric protein harbouring inserted Muc1 epitope to generate monoclonal antibodies against Muc1 epitope.

BALB/c mice were immunized with yeast-expressed purified recombinant chimeric protein: hamster polyoma virus major capsid protein VP1 (HaPyV-VP1) harbouring inserted Muc1 epitopes at positions 1 and 4 (VP1/Muc). The expression in yeast and properties of HaPyV-VP1 (VP1) protein were described previously [Gedvilaitė A., Frommel C., Sasnauskas K., et al., Virology. 2000, v. 273, n. 1, p. 21-35]. Mice were immunized by injecting subcutaneously 50 μg of VP1/Muc antigen mixed with complete Freund's adjuvant. Four weeks later mice were boosted in a similar way with 50 μg of VP1/Muc antigen in incomplete Freund's adjuvant. Four weeks later mice were boosted again with 50 μg of VP1/Muc antigen without an adjuvant. During immunization, the titers of antibodies specific to Muc1 epitope were tested by an enzyme-linked immunosorbent assay (ELISA). On day 3 after the last boost the hybridization was performed.

Spleen cells of the immunized mice were fused with mouse myeloma Sp 2/0 cells lacking an enzyme hypoxanthine phosphoribosyl transferase, non-proliferating in a selective HAT medium with hypoxanthine-aminopterin-thymidine ($10^{-4}$M hypoxanthine, $1{,}6\times10^{-5}$M thymidine, $4\times10^{-7}$M aminopterin), non-producing immunoglobulins nor their chains. Before fusion, the cells should be in a logarithmic growth phase. The fusion was performed by incubation the cells for 2 min with 50% polyethylene glycol solution (PEG-4000) in Dubecco modified Eagl's medium (DMEM) with 10% dimethylsulfoxide (DMSO). The ratio of myeloma and spleen cells during fusion was 1:5. After fusion, the cells were washed with serum-free DMEM, resuspended in a selective HAT medium and seeded into multiwell plates at a density $5\times10^5$ cells per well.

Hybrid clones appeared on days 5-10 after fusion. Growth medium was tested by an indirect ELISA for the antibodies specific to VP1/Muc protein. Every 4-5 days one-half of the growth medium was changed. For a first time HAT medium was changed to HT medium containing hypoxanthine-thymidine ($10^{-4}$ M hypoxanthine and $1{,}6\times10^{-4}$ M thymidine). Later on, HT medium was changed stepwise to normal growth medium. Hybrid clones producing antibodies specific to VP1/Muc were cloned by limiting dilution assay. The clones appeared on days 4-7 after cloning. They were tested by an indirect ELISA. Selected clones were propagated and then either cultivated in vitro, or frozen for a storage in liquid nitrogen.

7 hybridoma clones producing monoclonal antibodies (MAbs) against chimeric protein VP1/Muc were obtained. It was determined that 2 of them were specific to Muc1 peptide and 5 were specific to HaPyV-VP1 (carrier protein).

Hybridomas producing Mabs against Muc1 peptide were designed 12B2 and 14G2. They are stored under the respective storage numbers: 12B2—M05101, 14G2—M0502.

Control group of BALB/c mice was immunized with a synthetic Muc1 peptide chemically coupled to bovine serum albumin (BSA/Muc) using glutaraldehyde. Mice were immunized according to the scheme given above. During immunization, the titers of Muc1-specific antibodies were tested.

It was determined that BSA/Muc did not elicit an immune response against Muc1 peptide. Therefore, spleen cells of these immunized mice were not used for a fusion and production of monoclonal antibodies.

EXAMPLE 2

Determination of the specificity and isotypes of monoclonal antibodies raised against Muc1 epitope.

The specificity of antibodies produced by clones 12B2 and 14G2 was determined by ELISA and Western blotting. Immunoglobulin isotypes were determined by ELISA using antibody isotyping kit [Sigma, JAV].

It was determined by using these assays that monoclonal antibodies are of IgG isotype, IgG1 subtype and recognize both chimeric protein VP1/Muc and synthetic Muc1 peptide but do not react with VP1 (carrier protein). This suggests that they are specific to Muc1 epitope. The results are presented in Table 1 and FIG. 1.

The data on the specificity and isotypes of MAbs produced by hybridomas 12B2 and 14G2 are presented in Table 1.

TABLE 1

| | | Reactivity with: | | |
|---|---|---|---|---|
| Hybridoma clone | Subtype (subclass) | HaPyV-VP1 | VP1/Muc | Synthetic peptide Muc1 |
| 12B2 | IgG1 | − | + | + |
| 14G2 | IgG1 | − | + | + |

FIG. 1 shows Western blotting picture where recombinant proteins VP1 and VP1/Muc were immunostained with MAbs produced by hybridomas 12B2 and 14G2. In a comparison, Western blotting picture obtained with the same proteins immunostained with MAbs against VP1 protein are shown. MAb codes are indicated on the top of the picture:

12B2—against protein VP1/Muc;
14G2—against protein VP1/Muc;
9F11—against protein VP1,
6D11—against protein VP1.
Lane 1—VP1 protein; lane 2—VP1/Muc protein.

As demonstrated by Western blotting (FIG. 1), MAbs produced by hybridomas 12B2 and 14G2 react specifically with VP1/Muc protein but do not react with VP1 protein. As a control, MAbs 9F11 and 6D11 specific to VP1 protein were used. They react both with VP1 antigen and VP1/Muc antigen.

EXAMPLE 3

The use of chimeric protein harbouring an inserted fragment of hantavirus nucleocapsid protein to generate monoclonal antibodies against hantavirus nucleocapsid protein.

BALB/c mice were immunized with yeast-expressed recombinant chimeric proteins: HaPyV-VP1, harbouring inserted 120 amino acid-long fragment of Vranica hantavirus nucleocapsid protein at either position 1 or 4 (VP1/VR120). The expression of these proteins in yeast and their properties were described previously [A. Gedvilaite, A. Zvirbliene, J. Staniulis et al, Viral Immunol. 2004, 17(1):51-68].

Mice BALB/c were immunized 3 times and then the hybridization was performed. All procedures were performed in a similar way as described in Example 1 with the only difference that VP1/VR120 protein was used instead of VP1/Muc protein. During immunization, the titers (levels) of specific antibodies in the sera of immunized mice were tested, e.g., the development of IgG antibodies against the inserted fragment of hantavirus nucleocapsid protein (HN) was determined.

Figure 2:
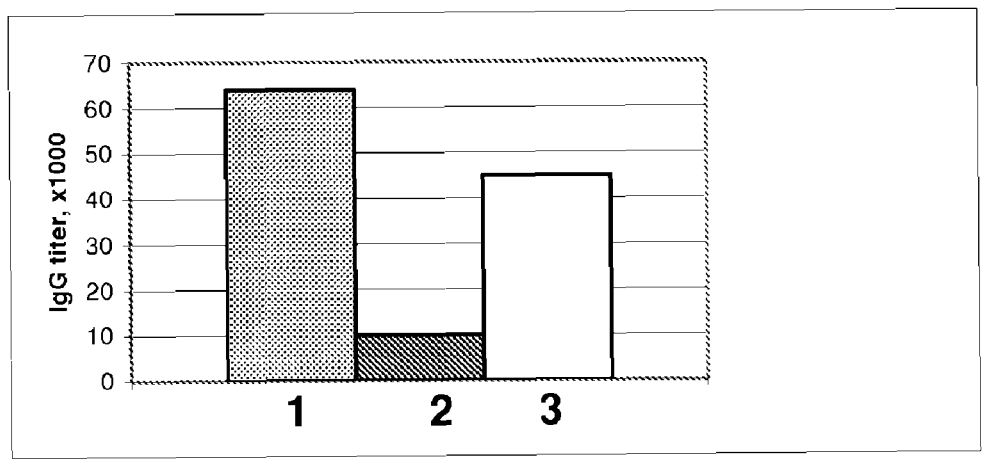

FIG. 2 demonstrates the immunogenicity of chimeric protein VP1/VR120. The titers of IgG antibodies in blood sera of immunized mice after the 3rd immunization are shown. The titers were determined by ELISA using the following antigens:
1—VP1/VR120;
2—VP1;
3—hantavirus nucleocapsid protein.

It was determined that antibody titers against HN protein are much higher that those against VP1 protein (FIG. 2).

After fusion, 4 hybridoma clones producing MAbs against chimeric protein VP1/VR120 were obtained. It was determined that all of them react with VP1/VR120 but do not react with VP1 (carrier protein). This suggests that all hybridomas generated are specific to the fragment of HN protein inserted into chimeric protein VP1/VR120.

Thus, it can be concluded that the insertion of HN fragment into VLPs significantly enhanced its immunogenicity. High titers of anti-HN antibodies in the sera of immunized mice suggest that inserted 120 amino acid-long fragment is displayed on the surface of chimeric protein and therefore more efficiently acivates B cells than VP1 carrier protein. Hybridoma technology is based on the generation and selection of B cell-tumor cell hybrids. Thus, in the case if the antigen acivates more B cells, more hybridomas producing MAbs against this particular antigen are generated. Generation of hybridomas specific exclusively to the inserted HN fragment but not to VP1 (carrier protein) can be explained in this way. These results suggest that the insertion of a protein fragment into VLPs is more efficient mean of hybridoma production than other previously described means such as peptide coupling with carrier proteins by chemical methods.

Hybridomas producing monoclonal antibodies against HN protein were designed 7A5, 5E11, 5C5, 2E6. Their storage numbers are: HN0501, HN0502, HN0503, HN0504, respectively.

EXAMPLE 4

Determination of specificity and isotypes of monoclonal antibodies raised against HN protein.

The specificity of antibodies produced by the obtained hybridomas was tested by ELISA and Western blotting using recombinant hantavirus proteins. Immunoglobulin isotypes were determined by ELISA as described in Example 2. It was determined by using these methods that all MAbs obtained are of IgG isotype. Their subtypes are IgG1, IgG2a and IgG2b.

The data on the specificity and isotypes of MAbs produced by hybridomas 7A5, 5E11, 5C5 and 2E6 are presented in Table 2.

TABLE 2

| Hybridoma clone | Subtype (subclass) | Reactivity with: | | |
|---|---|---|---|---|
| | | HaPyV-VP1 | HN | VP1/VR120 |
| 7A5 | IgG1 | − | + | + |
| 5E11 | IgG1 | − | + | + |
| 5C5 | IgG2a | − | + | + |
| 2E6 | IgG2b | − | + | + |

FIG. 3 illustrates the ability of MAbs produced by hybridomas 7A5, 5E11, 5C5 and 2E6 to recognize full-length hantavirus nucleocapsid protein. Western blotting picture of proteins immunostained with MAbs produced by hybridoma 7A5 is shown.

Lanes 1-9—nucleocapsid proteins of different hantaviruses.

It was determined by Western blotting that all MAbs recognize both chimeric protein VP1/VR120 and yeast-expressed nucleocapsid proteins of different hantaviruses. This suggests that the antibodies are functionally active and react with full-length HN proteins. Therefore, these MAbs might be used for the detection of HN proteins in biotechnology and/or diagnostics.

In Conclusion:

1) When VLPs with a short-sized fragment (9 aa-long Muc 1 epitope) were used for the immunization and generation of hybridomas, 2 hybridomas producing MAbs against this epitope and 5 hybridomas producing MAbs against HaPyV-VP1 (carrier protein) were obtained. Thus, the yield of hybridomas specific to the inserted fragment was higher than one could expect based on the ratio of Muc1 epitope size and VP1 carrier protein size (Muc1 epitope—9 aa, VP1—approximately 380 aa);

2) When VLPs with a long-sized fragment (120aa-long HN fragment) were used for the immunization and generation of hybridomas, only hybridomas producing MAbs against the inserted fragment but not to VP1 carrier were obtained. Thus, the yield of hybridomas specific to the inserted fragment (similarly as in point 1) was higher than one could expect based on the ratio of HN fragment size and VP1 carrier protein size (HN fragment—120 aa, VP1—approximately 380 aa).

EXAMPLE 5

Investigation of the reactivity of monoclonal antibodies raised against HN protein with native hantaviruses The ability of MAbs raised against HN protein to recognize native viral nucleocapsids was tested by immunofluorescence analysis of hantavirus-infected cells.

FIGS. 4a and b illustrates the ability of MAbs produced by hybridomas 5E11, 5C5, 7A5 and 2E6 to recognize native viral nucleocapsid in hantavirus-infected cells. The pictures were obtained by indirect immunofluorescence staining of cells infected with different hantaviruses: Puumala hantavirus (strain Vranica-Halnaas) and Seoul hantavirus. To prove the ability of MABs to recognize native hantaviruses, the slides with hantavirus-infected cells [EuroImmune, Germany] were immunostained with MAbs 5E11, 5C5, 2E6 and 7A5, then incubated with FITC-labeled anti-mouse IgG antibody and observed by fluorescent microscope Olympus IX-70 [Olympus, Japan]. All MAbs specifically reacted with hantavirus-infected cells (FIGS. 4a and b, A-F) and did not react with non-infected cells used as a negative control (FIG. 4b, G). An additional control experiment was performed with MAbs raised against recombinant full-length His-tagged HN protein (MAb clone 9H3). MAb 9H3 did not react with hantavirus-infected cells (FIG. 4b, H). Thus, MAbs raised against the fragment of HN protein inserted into VLPs recognize native viral nucleocapsids, In contrast, MAbs raised a recombinant full-length HN protein that underwent denaturation/refolding procedures do not react with native viral nucleocapsids. These data show that MAbs raised against the fragment of HN protein inserted into VLPs are directed to the epitopes present in native virus. This suggests that the fragment of HN protein inserted into VLPs is natively folded. Therefore, it elicits development of MAbs directed to the epitopes similar/identical to that present in native virus. These data demonstrate the advantages of chimeric VLPs over the traditional antigens such as full-length recombinant proteins.

In summary the invention describes the method to produce monoclonal antibodies by using recombinant chimeric proteins that self-assemble to virus-like particles. These viral proteins are used as carriers for peptides or epitopes, against which monoclonal antibodies are intended to produce. Chimeric viral proteins described here contain inserted foreign protein fragments (epitopes) at certain sites that are exposed on the surface of virus-like particles. These chimeric proteins are more immunogenic and more efficiently promote induction of monoclonal antibodies than the immunogens described previously. The invention belongs to the field of biotechnology and can be applied in hybridoma technology to generate monoclonal antibodies against desired epitopes.

The invention describes new hybridomas obtained by this process.

While the invention has been described in detail with reference to preferred embodiments thereof, it will be apparent to one skilled in the art that various changes can be made, and equivalents, employed, without departing from the scope of the invention. Each of the aforementioned documents is incorporated by reference herein in its entirety.

The invention claimed is:

1. A hybridoma having accession number DSM ACC2788, capable of producing monoclonal antibodies against a Muc1 epitope.

2. A hybridoma having accession number DSM ACC2787, capable of producing monoclonal antibodies against a hantavirus nucleocapsid protein.

3. A monoclonal antibody obtainable from the hybridoma of claim 1 or claim 2.

* * * * *